United States Patent
Min (10) Patent No.: US 10,635,899 B2
(45) Date of Patent: Apr. 28, 2020

(54) APPARATUS AND METHOD FOR DETECTING BRAIN FINGERPRINT USING CAUSAL CONNECTIVITY OF BRAINWAVE

(71) Applicant: Korea University Research and Business Foundation, Seoul (KR)

(72) Inventor: Byoung-Kyong Min, Seoul (KR)

(73) Assignee: Korea University Research and Business Foundation, Seoul (KR)

(*) Notice: Subject to any disclaimer, the term of this patent is extended or adjusted under 35 U.S.C. 154(b) by 338 days.

(21) Appl. No.: 15/677,589

(22) Filed: Aug. 15, 2017

(65) Prior Publication Data

US 2018/0053049 A1   Feb. 22, 2018

(30) Foreign Application Priority Data

Aug. 19, 2016 (KR) .......... 10-2016-0105488

(51) Int. Cl.
*G06F 21/32* (2013.01)
*G06K 9/00* (2006.01)
(Continued)

(52) U.S. Cl.
CPC ...... *G06K 9/00536* (2013.01); *A61B 5/04012* (2013.01); *A61B 5/0476* (2013.01); *A61B 5/04842* (2013.01); *A61B 5/103* (2013.01); *A61B 5/117* (2013.01); *G06F 21/32* (2013.01); *G06K 9/0053* (2013.01);
(Continued)

(58) Field of Classification Search
None
See application file for complete search history.

(56) References Cited

U.S. PATENT DOCUMENTS

| | | | | |
|---|---|---|---|---|
| 5,325,862 A | * | 7/1994 | Lewis | A61B 5/1171 600/544 |
| 2014/0020089 A1 | * | 1/2014 | Perini, II | G06F 21/32 726/19 |

(Continued)

FOREIGN PATENT DOCUMENTS

| KR | 1020040019013 A | 3/2004 |
|---|---|---|
| WO | WO-2014076698 A1 * | 5/2014 |

OTHER PUBLICATIONS

Gomez Herrero et al. Measuring directional coupling between EEG sources. NeuroImage 43 (2008) 497-508. (Year: 2008).*

(Continued)

*Primary Examiner* — Etsub D Berhanu
(74) *Attorney, Agent, or Firm* — Fox Rothschild LLP (57) ABSTRACT

When a brain fingerprint is detected, a predetermined visual stimuli is output on a screen of a display, causal connectivity formed by unique EEG signals of a subject between two or more brain regions from among a predetermined plurality of brain regions is detected on the basis of the EEG signals of the subject who selectively attends to a part corresponding to a letter or symbol conceived by the subject from among the visual stimuli output on the screen of the display, an activation pattern of causal connectivity between brain regions is recognized on the basis of the detected causal connectivity, and the subject is identified by using the recognized unique activation pattern of causal connectivity between brain regions as a brain fingerprint.

11 Claims, 6 Drawing Sheets
(2 of 6 Drawing Sheet(s) Filed in Color)

(51) Int. Cl.

| | |
|---|---|
| *A61B 5/0476* | (2006.01) |
| *A61B 5/0484* | (2006.01) |
| *A61B 5/04* | (2006.01) |
| *G06K 9/62* | (2006.01) |
| *A61B 5/103* | (2006.01) |
| *A61B 5/117* | (2016.01) |

(52) U.S. Cl.
CPC ....... *G06K 9/0055* (2013.01); *G06K 9/00496* (2013.01); *G06K 9/00523* (2013.01); *G06K 9/62* (2013.01); *G06K 9/6267* (2013.01)

(56) References Cited

U.S. PATENT DOCUMENTS

2014/0058483 A1* 2/2014 Zao .......................... A61N 5/06 607/88

2014/0188770 A1* 7/2014 Agrafioti ................ A61B 5/117 706/13

OTHER PUBLICATIONS

Khalifa et al. A Survey of EEG Based User Authentication Schemes. The 8th International Conference on INFOrmatics and Systems (INFOS2012)—May 14-16. (Year: 2012).*

Palaniappan. Method of identifying individuals using VEP signals and neural network. IEE Proc.-Sci. Meas. Technol., vol. 151, No. 1, Jan. 2004. (Year: 2004).*

Yazdani et al. Fisher Linear Discriminant Based Person Identification Using Visual Evoked Potentials. 2008 9th International Conference on Signal Processing. (Year: 2008).*

Marcel et al. Person Authentication Using Brainwaves (EEG) and Maximum a Posteriori Model Adaptation. IDIAP Research Report. (Year: 2005).*

* cited by examiner

APPARATUS AND METHOD FOR DETECTING BRAIN FINGERPRINT USING CAUSAL CONNECTIVITY OF BRAINWAVE

CROSS-REFERENCE TO RELATED APPLICATION

This application claims the benefit under 35 USC 119(a) of Korean Patent Application No. 10-2016-0105488 filed on Aug. 19, 2016, in the Korean Intellectual Property Office, the entire disclosures of which is incorporated herein by reference for all purposes.

TECHNICAL FIELD

The present disclosure relates to a brain fingerprint detecting apparatus and method for detecting a brain fingerprint by using causal connectivity of brainwaves.

BACKGROUND

Studies have continued to find out the meaning of each brainwave form by measuring electrical activity of the brain and thus obtaining a brainwave and detecting characteristics, such as frequency and amplitude, of the brainwave. Recently, brain fingerprint technology as one of the studies using brainwaves has been gaining a lot of attention but is still in its early stage.

In this regard, Korean Patent Laid-open Publication No. 10-2004-0019013 (entitled "Method and apparatus for brain fingerprinting, measurement, assessment and analysis of brain function") discloses a method of detecting information stored in the electronic signals originating in the brain. According to the above patent, the method of detecting information stored in the brain of a subject comprises: presenting to the subject with stimuli including: probe stimuli relevant to a situation under investigation for effecting in the subject a specific brain response when the subject has knowledge thereof, irrelevant stimuli not relevant to the situation, and target stimuli having at least one of the following characteristics: they are identified to the subject as being noteworthy; and they are relevant to the situation under investigation; assigning a task that involves discriminating between target stimuli and standard stimuli and communicating this discrimination through an overt response; detecting an electrical brain response from the subject in response to each of the stimuli; analyzing the electrical brain responses for uncovering the specific brain response therein; and comparing the electrical brain responses due to the probe, irrelevant, and target stimuli for detecting the presence or absence of the information in the subject's brain based on the presence or absence of the specific brain response in response to the probe stimuli.

As such, the conventional brain fingerprint technology has a limitation in that electroencephalographic (EEG) signals are simply used as conditions for inference of a subject's condition, whether the subject told a lie or not, or certain information stored in the brain.

Meanwhile, various technologies of processing brain-machine interfaces by analyzing parameters caused by cognitive properties of EEG signals have been developed. As a cognitive property of EEG signals, an event-related potential (ERP) which is a brain potential generated in relation to a presented stimulus or event may be used. A demand for brain fingerprint technology capable of using the ERP as unique identification information for identifying a subject, such as fingerprint (i.e., brain fingerprint) and a method of applying the brain fingerprint technology to an actual brain-machine interface has been increased.

SUMMARY

In view of the foregoing, the present disclosure provides a brain fingerprint detecting apparatus and method of detecting a specific cognitive component of a brainwave which is different from each other between subjects and recognizing the specific cognitive component as a brain fingerprint.

However, problems to be overcome by the present disclosure are not limited to the above-described problems. There may be other problems to be solved by the present disclosure.

According to an aspect of the present disclosure, an apparatus for detecting a brain fingerprint includes: a display that outputs predetermined visual stimuli; a memory configured to store a brain fingerprint detecting program for identifying subjects by detecting a brain fingerprint of each subject on the basis of EEG signals of the subject who selectively watches at least a part of the visual stimuli; and a processor that executes the program stored in the memory. Herein, in response to execution of the brain fingerprint detecting program, the processor is configured to detect causal connectivity between two or more brain regions among a plurality of brain regions on the basis of the EEG signals, determine a brain fingerprint of the subject by recognizing an activation pattern of the causal connectivity between brain regions on the basis of the causal connectivity, and identified the subject based on the determined brain fingerprint.

Further, according to another aspect of the present disclosure, a method for detecting a brain fingerprint using the apparatus for detecting a brain fingerprint includes: outputting predetermined visual stimuli on a screen of a display; detecting causal connectivity between two or more brain regions among a plurality of brain regions on the basis of EEG signals of a subject who selectively watches at least a part of the visual stimuli output on the screen of the display; determining a brain fingerprint of the subject by recognizing an activation pattern of causal connectivity between brain regions on the basis of the detected causal connectivity of task-driven source-level EEG signals; and identifying the subject based on the determined brain fingerprint.

According to any one of the aspects of the present disclosure, a unique causal connectivity pattern of brainwaves of each user is recognized and used as a brain fingerprint, and, thus, it is possible to accurately identify a plurality of users with only unique causal connectivity of the user's brainwaves generated when the user intentionally watches a selective part of visual stimuli.

Further, according to any one of the aspects of the present disclosure, a flickering line array is implemented as brainwave-inducing visual stimuli, and, thus, it is possible to readily implement a visual stimulation means in various devices required to identify users and thus possible to easily link a brain fingerprint detecting apparatus with other devices.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items. The patent or application file contains at least one drawing executed in color. Copies of this patent or patent application publication with color drawing(s) will be provided by the Office upon request and payment of the necessary fee.

DETAILED DESCRIPTION

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "unit" or "module" includes a unit implemented by hardware or software and a unit implemented by both of them. One unit may be implemented by two or more pieces of hardware, and two or more units may be implemented by one piece of hardware.

Figure 1:
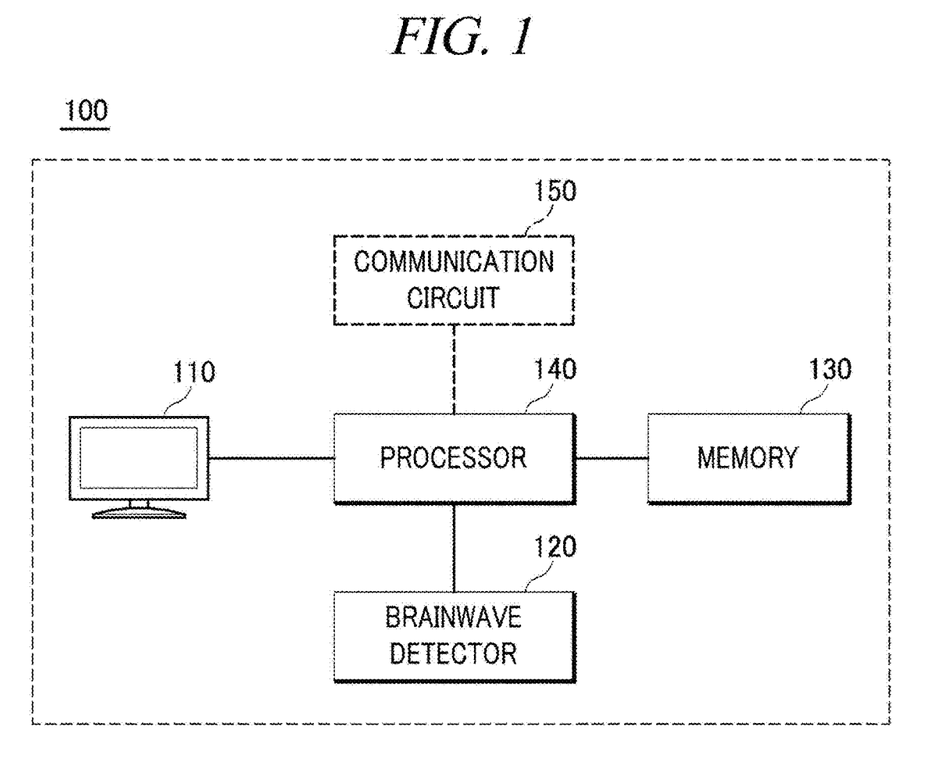
FIG. 1 illustrates a configuration of a brain fingerprint detecting apparatus.

FIG. 1 illustrates a configuration of a brain fingerprint detecting apparatus. Further, FIG. 2 illustrates an example of a visual stimuli line array.

As illustrated in FIG. 1, a brain fingerprint detecting apparatus 100 includes at least one of a display 110, a brainwave detector 120, a memory 130, and a processor 140. Further, the brain fingerprint detecting apparatus 100 may further include a communication circuit 150 capable of transmitting/receiving signals to/from various other devices interworking with the brain fingerprint detecting apparatus 100.

The display 110 outputs visual stimuli that induce a subject to generate a specific brainwave under the control of the processor 140.

In this case, the display 110 may output a line array including two or more lines respectively flickering at predetermined frequencies on the screen. The line array may be displayed fully or in a predetermined size on the screen of the display 110. In this case, a size of the line array output on the display 110 may be designed without need for a macroscopic eye-movement of a subject who watches the display 110. Further, a position where the display 110 is installed may be designed at an appropriate distance without need for a macroscopic eye-movement of the subject. The display 110 may include all devices or means, such as a LCD (liquid crystal display) device, a LED (light emitting diode) device, and a touch screen, capable of outputting a light emitting line on the screen regardless of material and size.

Meanwhile, in some scenarios, the display 110 may be a component of an external display device (not illustrated) separate from the brain fingerprint detecting apparatus 100. In this case, the brain fingerprint detecting apparatus 100 may supply a control signal to the external display device (not illustrated) to enable the visual stimuli to be output.

The brainwave detector 120 is configured to measure EEG signals of the subject who watches the visual stimuli output on the display 110. In this case, the brainwave detector 120 may be configured to measure a steady state visual evoked potential (SSVEP) generated from the brain of the subject.

The brainwave detector 120 may measure EEG signals via contact or non-contact measurement. The kind of a measurement method is not limited thereto, and various methods may be used. Further, the brainwave detector 120 may be a brainwave measuring device itself including a measuring means such as a brainwave measuring electrode, or may be connected to a brainwave measuring device to obtain EEG signals measured by controlling an operation of the brainwave measuring device. In this case, a configuration of the brain fingerprint detecting apparatus 100 including the brainwave detector 120 may be implemented as being integrated with the brainwave measuring device. For example, the brainwave measuring device may be implemented as a headset form in which brainwave measuring means (i.e., measuring electrodes) are installed at a plurality of positions.

The brainwave detector 120 measures intensities of EEG signals from a predetermined plurality of brain regions of the subject continuously on the time axis. In this case, the brainwave measuring means of the brainwave detector 120 may operate at conventional positions respectively corresponding to the predetermined plurality of brain regions in the brain of the subject. For example, the brainwave detector 120 may apply the international 10-10 sensor placement system to measure EEG signals from a predetermined plurality of channels in the brain of the subject.

For reference, if the subject watches the grid-shaped flickering line array output (FIG. 2A) on the display 110 while attending to a combination of flickering lines corresponding to a certain intended shape among a predetermined plurality of shapes, EEG signals having the same spectral characteristics induced by attended flickering lines corresponding to the shape conceived by the subject may be dominantly detected. In this case, a plurality of brain regions measuring EEG signals may be set in a predetermined manner.

The memory 130 is configured to store a brain fingerprint detecting program for identifying a subject by detecting a unique causal connectivity patterns of each subject used as his/her brain fingerprint on the basis of EEG signals measured by the brainwave detector 120. For reference, the memory 130 collectively refers to a non-volatile storage device that retains information stored therein even when power is not supplied and a volatile storage device that requires power to retain information stored therein.

The processor 140 executes the program stored in the memory 130 to perform processes according to the program.

In response to execution of the brain fingerprint detecting program, the processor 140 performs the following processes (or operations).

The processor 140 may supply a control signal for outputting predetermined visual stimuli on the display 110. In this case, the visual stimuli may be a grid-shaped flickering line array output on the screen, and each line of the line array may flicker at a different frequency (for example, FIG. 2A).

For reference, the line array is designed to induce EEG signals of the subject through visual stimuli and each line may emit a light at a uniform luminance (e.g., mean luminance 136 cd/m$^2$). In this case, each line may be displayed in any one of red or green. This is because cone cells which are relatively large in number in the fovea of the retina of the human eye are cells sensing red and green. Further, each line of the line array may also be displayed in white or gray in order to use rod cells widely distributed in the greater part of the retina. Besides, each line of the line array may be displayed in any color which can be visually recognized.

Further, the lines may be arranged with a predetermined distance. In this case, a distance between the lines is psychophysically significant and can be previously set on the basis of the result of experiments. That is, the lines are arranged with a predetermined distance for a sufficient optical resolving power between the lines. For example, the distance between the lines may be set such that a visual angle depending on a maximum size (or length) of the line array is 8° to 10° or less in order for lights of all the lines to be intactly detected by the optic nerve without falling of an image on the retina to a blind spot. That is, the distance between the lines may be set such that visual stimuli caused by the line array do not reach the blind spot area in the retina of the subject but fall on the center of the fovea area where a visual information process is performed in the most sophisticated manner.

For example, two or more lines of the line array may be arranged in a grid shape. That is, as shown in FIG. 2, grid-shaped two or more lines may be arranged in the line array.

Figure 2A:
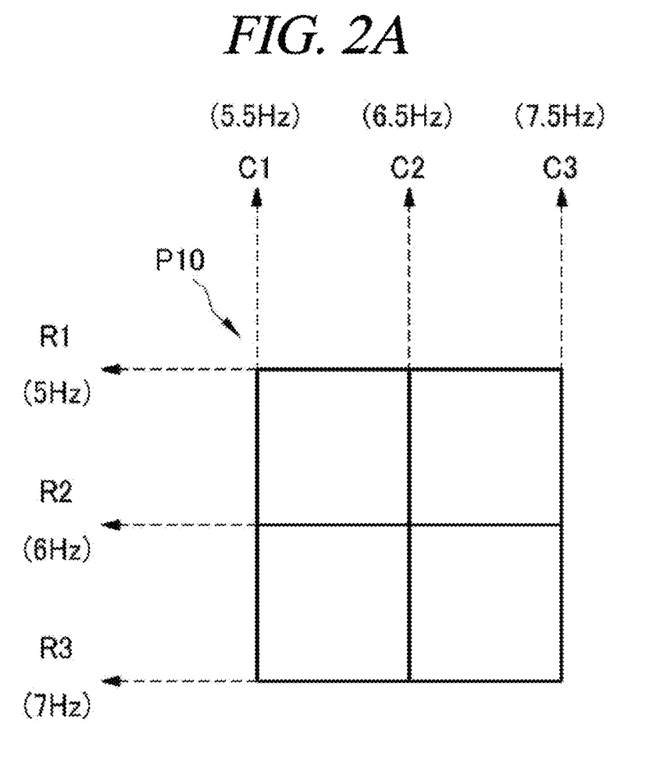
FIGS. 2A and 2B (collectively referred to as "FIG. 2") illustrates an example of a visual stimuli line array.
Figure 2B:
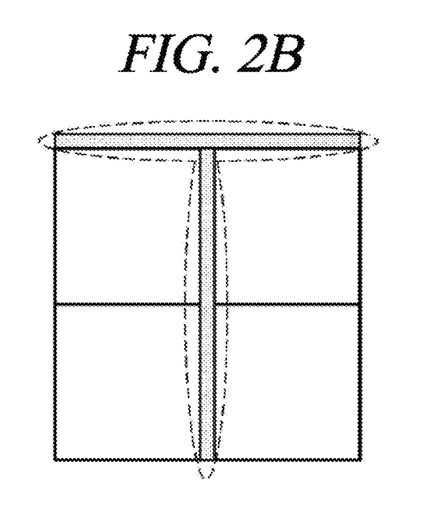

FIG. 2A and FIG. 2B show that a line array P10 includes 3 rows (R1 to R3) and 3 columns (C1 to C3) arranged in a matrix. As such, the line array P10 includes a plurality of rows and columns each flickering at a different frequency, and each row or column may be arranged to intersect with one or more columns or rows and the rows or the columns are spaced at a predetermined distance from each other.

The 3×3 grid-shaped line array can be implemented in a super-small size and can also express various shapes (e.g., letters and numbers) therein, and, thus, can be readily applied to any device. However, a shape of the line array and the number of lines included therein according to the present disclosure are not limited thereto. As the number of lines included in the line array is increased, the number of shapes which can be conceived by the subject is increased. Thus, the subject can conceive more detailed, more letter-like and various shapes.

Further, a plurality of flickering frequencies may be randomly assigned to the respective lines of the line array. For example, a flickering frequency may be set to a frequency (e.g., 5 Hz to 7.5 Hz) effective in inducing a steady state visual evoked potential (SSVEP) from among the EEG signals of the subject. For reference, a SSVEP is a component using brainwaves responsive to a repetitive visual stimulus. For example, while the subject watches a flickering stimulus, a brainwave having the same frequency as a flickering frequency of the stimulus is physically driven.

FIG. 2A shows that in the line array P10, the first row R1, the second row R2, and the third row R3 are set to flicker at 5 Hz, 6 Hz, and 7 Hz, respectively. Further, FIG. 2A shows that in the line array P10, the first column C1, the second column C2, and the third column C3 are set to flicker at 5.5 Hz, 6.5 Hz, and 7.5 Hz, respectively. As such, all the lines in the line array P10 are set to have different flickering frequencies from each other.

Furthermore, the flickering frequencies set for the lines in the line array P10 are maintained, and the flickering stimulus may continue in all of the rows and the columns.

While all the lines included in the line array continuously flicker at their own flickering frequencies, respectively, as shown in FIG. 2A, if the subject pays particular attention to lines corresponding to a certain shape (e.g., "T-shape") as shown in FIG. 2B, the leading characteristic of brainwaves of the subject corresponds to flickering frequency components of the first row R1 and the second column C2 or combinations thereof. The shapes (e.g., letters) which can be conceived by the subject may include any shape which can be formed by combination within the grid-shaped line array.

For reference, the flickering frequencies for the respective lines are set to higher frequencies and thus can reduce eye fatigue of the subject, and all of the lines may be set to have the same luminance in order to exclude any confounding effect possibly caused by a difference in luminance between lines.

Referring to FIG. 1 again, when the subject watches visual stimuli output on the display 110 while conceiving of a certain shape, the processor 140 receives EEG signals measured by the brainwave detector 120 from the subject. Then, the processor 140 detects EEG causal connectivity between two or more brain regions (e.g., Brodmann area) from among a predetermined plurality of brain regions on the basis of the measured EEG signal.

In this case, the processor 140 performs an EEG source localization analysis on the basis of the sensor-level EEG signals measured from the predetermined plurality of brain regions. For reference, the EEG signals processed by the processor 140 are brainwaves generated when the subject attends to a combination of specific lines of visual stimuli on the display 110 while conceiving of a predetermined shape, which causes significant differences in brainwave depending on an individual cognitive attribute of each user. Thus, it is possible to detect an activated brain region from among the plurality of brain regions of the subject attending to a specific combination of flickering lines in the line array on the display 110. Further, the processor 140 sequentially selects two or more brain regions having the prominent causal connectivity from the activated brain region among the plurality of the brain regions.

Specifically, the EEG signals measured by the brainwave detector 120 may be sensor-level signals measured from the scalp of the subject. The processor 140 converts the measured sensor-level EEG signals into source-level EEG signals of an original source area in the brain and then performs an analysis.

In this case, the processor 140 may convert the sensor-level EEG signals measured from the plurality of regions of the scalp into EEG source activity signals via at least one of low resolution electromagnetic tomography (LORETA), cortical current density source model, and other types of EEG source localization methods, and then obtain the source-level EEG signals. Then, in response to the estimated source-level EEG signals, the processor 140 selects the most activated two or more brain cortical regions on the basis of the degrees of source activity of the brain regions. In this case, the degree of EEG source activity may be determined on the basis of power or amplitude of a signal.

For reference, activity of various (sub)cortical regions in the brain may cause electromagnetic activity of the scalp region, and, thus, it may be estimated that activities of different scalp regions are generated due to different configurations and combinations of various brain regions. Therefore, an inverse program may be used to identify a source counterpart of a brainwave, and, thus, it is possible to compute a source signal (i.e., source level) corresponding to a brainwave (i.e., sensor level) on the scalp region. The inverse program is a technique capable of computing the degree of functional activity or degradation in the brain cortical areas using scalp-level signals. For example, a dipole model and a distributed source model may be used. In some scenarios, for example, the low resolution electromagnetic tomography (LORETA) as one of the distributed source models or the cortical current density source model is used. Thus, it is possible to compute a source-level signal in activated brain cortical areas, corresponding to a scalp-level brainwave of the subject and the degree of activity.

Then, the processor 140 analyzes directional causal connectivity over time between the selected two or more brain regions and thus detect causal connectivity between the selected two or more brain regions.

brain regions via Granger causality method to detect causal connectivity between the selected two or more brain regions. For reference, the Granger causality analysis makes it possible to determine whether or not there is causality between two phenomena. The processor 140 detects directional causality (i.e., causal connectivity) between two or more activated brain regions of the subject. For example, the processor 140 may obtain the degree of causal connectivity via a directed transfer function by applying a multivariate autoregressive model to EEG signals collected from a plurality of scalp sensors.

FIG. 3 illustrates activated regions depending on a brainwave of each subject and causal connectivity between the activated regions.

Figure 3A:
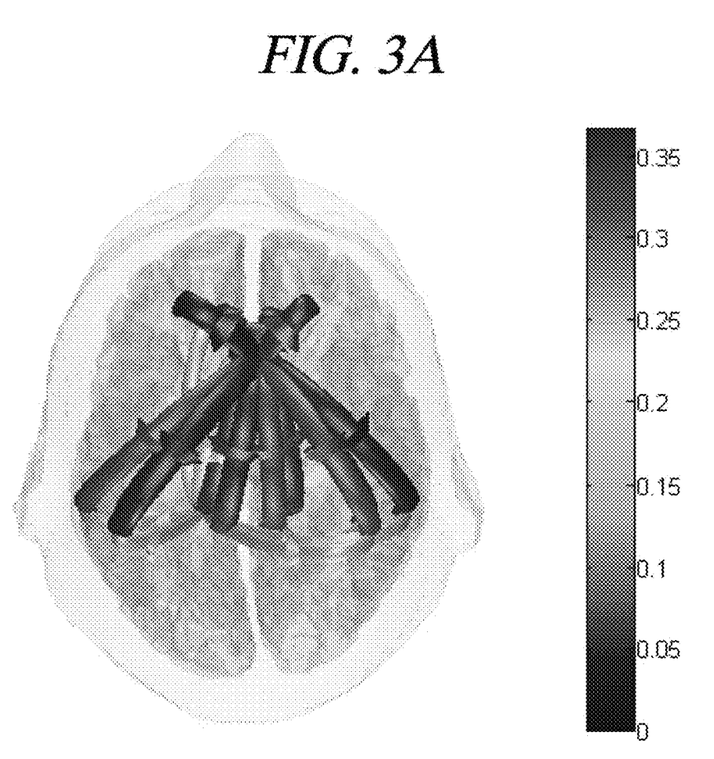
FIGS. 3A and 3B (collectively referred to as "FIG. 3") illustrates activated regions depending on a brainwave of each subject and causal connectivity between the activated regions.

FIG. 3A shows the degree of causal connectivity (noted as a color of arrows) between brain regions of the subject, and the direction of the causal connectivity (noted as a direction of arrows) between the brain regions.

Figure 3B:
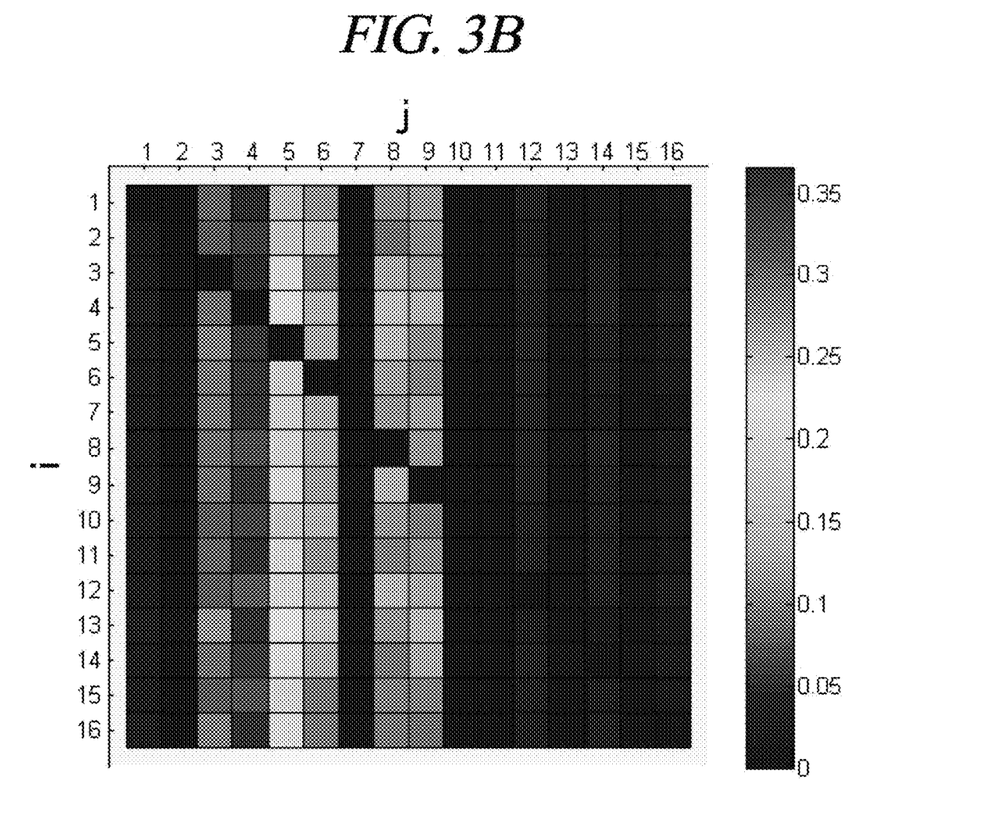

In FIG. 3B, "directional connectivity" between activated brain regions analyzed via Granger causality method is displayed as a matrix of pixels. That is, the degree of causal connectivity in a direction from j to i is displayed by colors. For reference, in the matrix of pixels as shown in FIG. 3B, each number on the i-axis and j-axis represents predetermined Brodmann areas.

As shown in FIG. 3A and FIG. 3B, if subjects conceive of a certain shape while attending to flickering visual stimuli, unique causal connectivity patterns of individual's brain regions for each subject can be efficiently distinguished. Therefore, causal connectivity between activated brain regions is different from each other. For example, under the same measurement conditions, a first brain region and a second brain region of a first subject may be most activated and the sequence of activation may have causal connectivity with a certain directionality. Meanwhile, if brain regions of a second subject different from those of the first subject are most activated or even if brain regions of the second subject corresponding to those of the first subject are activated, the second subject has unique causal connectivity different from that of the first subject due to a difference in the degree of activation or directionality. That is, each subject has unique causal connectivity and the processor 140 recognizes individual causal connectivity for each subject as an activation pattern of causal connectivity between brain regions (hereinafter, referred to as "brain region activation pattern").

Referring to FIG. 1 again, the processor 140 determines a brain fingerprint of the subject by recognizing a brain region activation pattern on the basis of the causal connectivity corresponding to the measured EEG signals and identifies the subject using the brain fingerprint.

In this case, the processor 140 learns at least one classifier. The processor 140 previously performs machine learning of a brain region activation pattern labeled for a predetermined condition of brainwave generation caused by visual stimuli to each of a plurality of subjects. Further, the processor 140 classifies an already registered user or a new user by distinguishing a brain region activation pattern caused by an EEG signal of a present subject through the classifier. In this case, if the subject is a user whose brain region activation pattern is previously machine-learned (i.e., already registered user), the processor 140 can identify a user corresponding to the subject from among already registered users. Further, even if the subject is a new subject whose brain region activation pattern is not previously machine-learned, the processor 140 can identify the subject as a new user through the classifier on the basis of information stored via previous machine learning.

Further, the brain fingerprint detecting apparatus 100 may interwork with various other devices required to identify users. In this case, as shown in FIG. 1, the brain fingerprint detecting apparatus 100 further includes the other devices interworking therewith and the communication circuit 150 configured to transmit/receive various signals (data).

For example, a doorlock which is one of security devices may be applied as a device interworking with the brain fingerprint detecting apparatus 100 or included in the brain fingerprint detecting apparatus 100. For reference, the doorlock includes a means (not illustrated) for opening/closing a door and may further include a control module (not illustrated) for controlling an operation of the opening/closing means and a communication circuit (not illustrated) for transmitting/receiving data to/from the processor 140 of the brain fingerprint detecting apparatus 100. Further, the display 110 of the brain fingerprint detecting apparatus 100 may also be implemented on the interworking device.

In this case, the processor 140 may be configured to determine whether or not the present subject is a permitted user, as a result of identifying the subject on the basis of EEG signals of the subject. Then, if the subject is a permitted user, the processor 140 may transmit a user authentication signal (i.e., door open signal, etc.) to the doorlock (not illustrated) through the communication circuit 150.

Further, the brain fingerprint detecting apparatus 100 may be mounted on a remote controller of home appliance such as a TV. In this case, the display 110 may be small-sized liquid crystal screen mounted on the remote controller or a screen of the home appliance connected to the remote controller. If a certain user conceives of an intended shape (i.e., letter, number, symbol, etc.) while watching a line array on the small-sized liquid crystal screen of the remote controller or the screen of the home appliance, the brain fingerprint detecting apparatus 100 may identify the user by measuring and analyzing brainwaves of the user and perform various control operations depending on a result of the identification.

Therefore, the user can perform user authentication to various interworking devices and control the devices just by conceiving of a specific shape or letter.

A process of identifying a subject by recognizing a causal connectivity pattern of brainwaves as described above will be described in detail with reference to FIG. 4.

Figure 4:
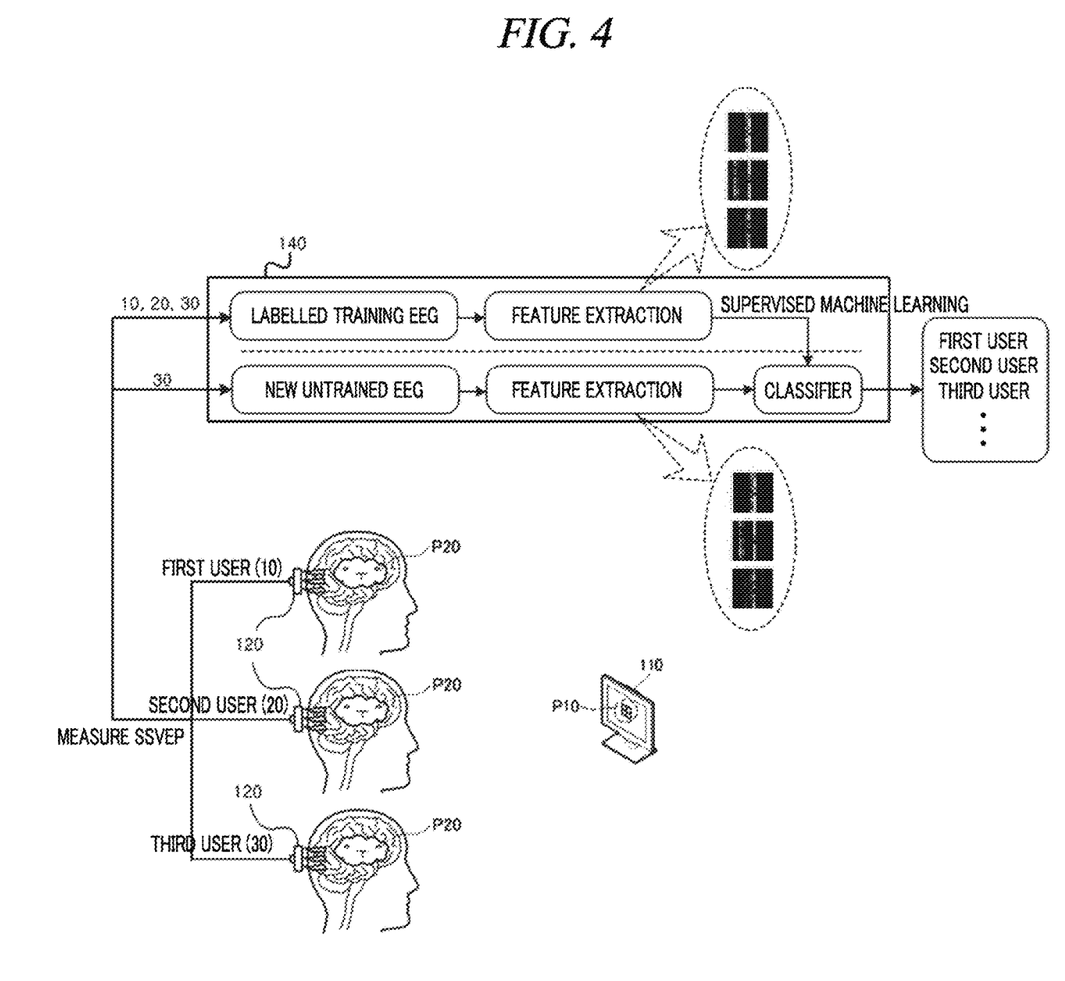
FIG. 4 is a conceptual diagram provided to explain a brain fingerprint detecting process using causal connectivity of brainwaves.

FIG. 4 is a conceptual diagram provided to explain a brain fingerprint detecting process using causal connectivity of brainwaves.

As illustrated in FIG. 4, the processor 140 performs an initial process in order for a plurality of subjects to learn a brain region activation pattern of causal connectivity for certain reference shapes before performing a process of analyzing EEG signals of a subject to identify the target subject. That is, the processor 140 performs machine learning of a feature extracted from labeled training EEG signals measured from each of the plurality of subjects and then performs calibration of setting a standard value for a classifier.

In this case, a grid-shaped line array flickering at a predetermined flickering frequency may be output on the screen. FIG. 4 shows first to third users 10, 20, and 30 as the plurality of subjects, and the number of subjects is not limited. That is, the number of subjects who previously learns a brain region activation pattern of causal connectivity may be 1 or more depending on the purpose of identification of a subject.

Then, the processor 140 measures spectral components of EEGs in a state where the processor 140 already knows a specific shape (i.e., reference shape) conceived by the subject. As such, the shape conceived by the subject is labeled with the measured EEG spectral components.

Then, the processor 140 extracts a feature on the basis of the labeled training EEG signals. In this case, the processor 140 detects the most activated two or more brain regions of the subject on the basis of the labeled training EEG signals and extracts causal connectivity between the assigned brain regions as a feature.

Further, the processor 140 recognizes brain region activation patterns of causal connectivity via machine learning (or supervised machine learning) of features extracted from the respective subjects. In this case, the processor 140 may function to perform an operation of a support vector machine (SVM) as a classifier for learning a brain region activation pattern of causal connectivity or an operation of a multi-class vector machine such as linear discriminant analysis (LDA) or deep-learning.

As described above, after a classifier that performs machine learning of a labeled EEG signal for each reference shape to a plurality of subjects is generated, the processor 140 receives an EEG signal for identifying an unknown arbitrary subject.

That is, as illustrated in FIG. 4, the processor 140 receives a newly measured EEG signal (new untraining EEG signal) from a new subject or an already-registered subject but arbitrary-chosen as a test subject (e.g., an input of a brainwave of the third user 30 in FIG. 4) through the brainwave detector 120.

In this case, if the subject conceives of a T-shape P20 while attending to the grid-shaped flickering line array P10 output on the screen of the display 110, the processor 140 may extract a causal connectivity feature between brain regions corresponding to the T-shape from the new untraining EEG signal.

The processor 140 inputs the feature extracted from the new untraining EEG signal (i.e., EEG signals of the third user 30) into the classifier and identifies a subject matched with the feature. As a result, a brain region activation pattern corresponding to the causal connectivity feature input into the classifier is detected as a brain fingerprint. That is, as illustrated in FIG. 4, the test subject is correctly classified as the target subject (i.e., the third user).

Hereinafter, a method for detecting a brain fingerprint using the brain fingerprint detecting apparatus 100 will be described in detail with reference to FIG. 5.

Figure 5:
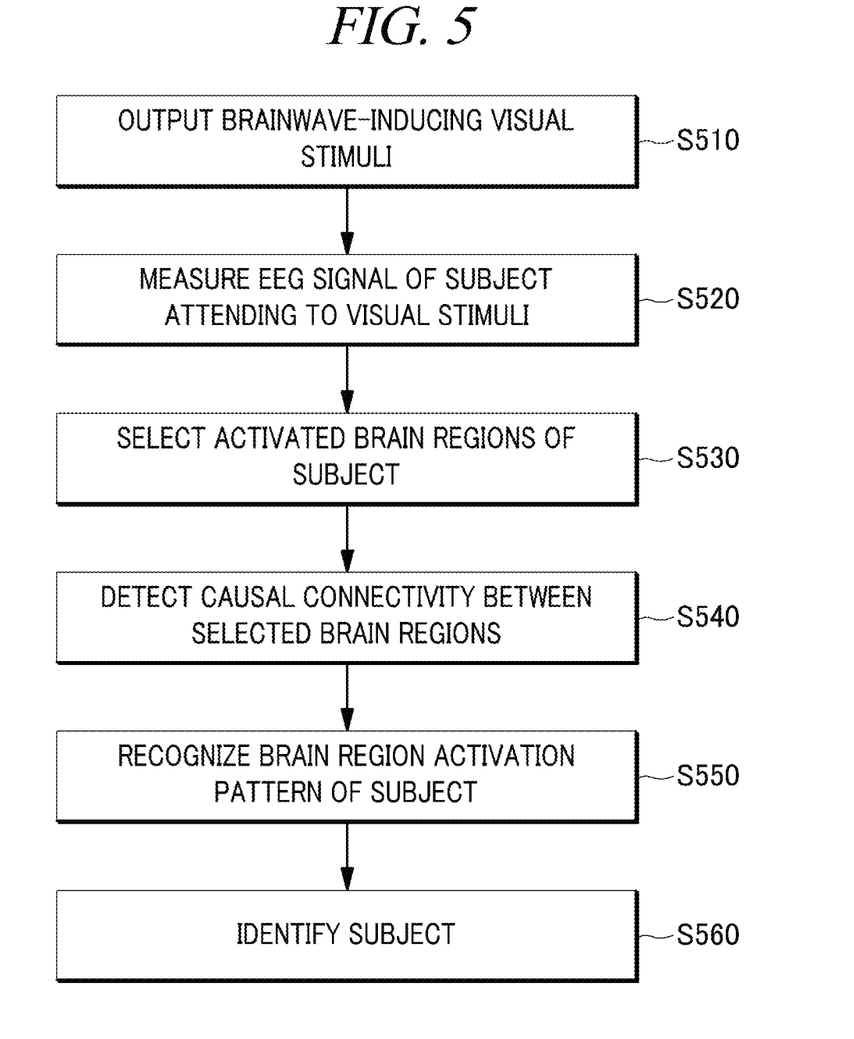
FIG. 5 is a flowchart provided to explain a method for detecting a brain fingerprint.

FIG. 5 is a flowchart provided to explain a method for detecting a brain fingerprint.

Firstly, the brain fingerprint detecting apparatus 100 outputs brainwave-inducing visual stimuli on the display which a subject is watching (S510).

In this case, the visual stimuli output on the display may be a grid-shaped flickering line array including a plurality of lines respectively flickering at predetermined flickering frequencies. The flickering lines in the grid-shaped line array may be set to have different flickering frequencies from each other, and two or more lines of the line array may be arranged in a grid shape. Further, a predetermined brainwave may be induced by the visual stimuli, and a frequency for the visual stimuli may be set to induce the predetermined brainwave.

Then, the brain fingerprint detecting apparatus 100 measures an EEG signal of the subject who watches the visual stimuli (S520).

In this case, the visual stimuli may be a line array including a plurality of flickering lines, and an EEG signal of a subject attending to a specific line combination of the flickering visual stimuli can be detected. For reference, grid-shaped two or more lines may be arranged in the line array. The EEG signal measured as such is an EEG signal induced when the subject attends to the flickering visual stimuli while conceiving of any one of predetermined shapes or letters.

Then, the brain fingerprint detecting apparatus 100 selects two or more activated brain regions of a subject corresponding to the measured EEG signal (S530).

Specifically, the brain fingerprint detecting apparatus 100 uses a sensor-level EEG signal measured from each of a predetermined plurality of brain scalp regions and performs EEG source localization on the basis of the detected signals to sequentially select two or more brain cortical regions from the most activated source-level brain region. In this case, the brain fingerprint detecting apparatus 100 may select two or more dominantly activated brain cortical regions by analyzing the EEG signals measured from the plurality of brain regions via, for example, low resolution electromagnetic tomography (LORETA) or cortical current density source model.

Then, the brain fingerprint detecting apparatus 100 is configured to directional connectivity over time between the selected two or more brain regions and thus detect causal connectivity between the selected two or more brain regions (S540).

In this case, the brain fingerprint detecting apparatus 100 may analyze the EEG signals of the selected two or more brain regions via Granger causality method to detect causal connectivity between the selected two or more brain regions.

Then, the brain fingerprint detecting apparatus 100 determines a fingerprint of the subject by recognizing brain region activation patterns of causal connectivity of target subject during the task performance on the basis of the detected causal connectivity (S550).

Then, the brain fingerprint detecting apparatus 100 identifies the target subject using the determined brain fingerprint (S560).

Herein, the above-described S510 to S550 are previously performed to a plurality of subjects and thus reach a state where machine learning is achieved, and, thus, a kind of classifier is generated. Therefore, the above-described S560 is performed by a classifier based on the already-acquired EEG activation patterns of casual connectivity between brain regions which are labeled for a predetermined condition including the generation of a predetermined brainwave via visual stimuli to each of a plurality of the subjects. Specifically, the brain fingerprint detecting apparatus 100 classifies an already registered user or a new user by distinguishing the EEG causal connectivity patterns across predetermined brain regions of a present subject through the classifier. In this case, if the subject is a user whose brain region activation pattern of causal connectivity is previously machine-learned (i.e., already registered user), the brain fingerprint detecting apparatus 100 can identify a user corresponding to the target subject from among already registered users. Further, even if the subject is a new subject whose brain region activation pattern of causal connectivity is not previously machine-learned (trained), the brain fingerprint detecting apparatus 100 can identify the subject as a new user through the classifier on the basis of information stored via previous machine learning. For reference, the predetermined condition may be set to various shapes which can be conceived by the subject who is selectively attending to at least a part (i.e., at least two lines) of the flickering visual stimuli. For example, the classifier may perform an operation such as a support vector machine (SVM), linear discriminant analysis (LDA), and deep-learning.

Meanwhile, the method for detecting a brain fingerprint may be performed via interworking with various other devices.

For example, if the method for detecting a brain fingerprint is applied to a door-lock, the method may further include determining whether or not the subject is a user permitted to use the door-lock according to a result of identification on the basis of brainwaves and transmitting a door open signal to the door-lock if the subject is determined as a permitted user, after S560.

An interworking device to which the method for detecting a brain fingerprint of the present disclosure is applied is not limited to the door-lock. The brainwave detector 120 may be a brainwave measuring device itself may also use a result of identification of a subject as a condition for the control of a certain process (or operation).

The above-described apparatus and method for detecting a brain fingerprint can be embodied in a storage medium including instruction codes executable by a computer such as a program module executed by the computer. Besides, the data structure can be stored in the storage medium executable by the computer. A computer-readable medium can be any usable medium which can be accessed by the computer and includes all volatile/non-volatile and removable/non-removable media. Further, the computer-readable medium may include all computer storage and communication media. The computer storage medium includes all volatile/non-volatile and removable/non-removable media embodied by a certain method or technology for storing information such as computer-readable instruction code, a data structure, a program module or other data. The communication medium typically includes the computer-readable instruction code, the data structure, the program module, or other data of a modulated data signal such as a carrier wave, or other transmission mechanism, and includes information transmission mediums.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

EXPLANATION OF REFERENCE NUMERALS

100: Brain fingerprint detecting apparatus
110: Display
120: Brainwave detector
130: Memory
140: Processor
150: Communication circuit

I claim:

1. An apparatus for detecting a brain fingerprint comprising:
   a memory configured to store a brain fingerprint detecting program for identifying a subject by detecting a brain fingerprint of the subject on the basis of EEG signals of the subject who selectively attends to at least a part of visual stimuli;
   a communication circuit configured to transmit/receive a signal to/from a security device interworking with the apparatus for detecting a brain fingerprint; and
   a processor that executes the program stored in the memory,
   wherein in response to execution of the brain fingerprint detecting program, the processor is configured to detect causal connectivity between two or more brain regions among a plurality of brain regions on the basis of the EEG signals, determine a brain fingerprint of the subject by recognizing an activation pattern of the causal connectivity between the two or more brain regions on the basis of the causal connectivity, and identify the subject based on the determined brain fingerprint;
   wherein the detecting of causal connectivity includes performing an EEG source localization analysis on the basis of the EEG signals measured from the plurality of the brain regions, and sequentially selecting two or more brain regions having the highest causal connectivity from activated brain regions among the plurality of the brain regions; and
   wherein the processor is configured to determine whether or not the subject is a permitted user on the basis of the identified brain fingerprint of the subject, and transmit an authentication signal to the security device through the communication circuit if the subject is a permitted user.

2. The apparatus for detecting a brain fingerprint of claim 1,
   wherein the processor is configured to machine-learn a classifier based on already-acquired activation patterns of casual connectivity between brain regions which are labeled for a predetermined condition to each of a plurality of subjects, wherein the predetermined condition includes the generation of a predetermined brainwave via visual stimuli, and classify a registered user or a new user by distinguishing the activation pattern of casual connectivity between brain regions of the subject or identify a user corresponding to the subject from among already registered users through the classifier.

3. The apparatus for detecting a brain fingerprint of claim 1,
wherein the processor is configured to convert the EEG signals measured from the plurality of the brain regions of the subject's scalp into source-level EEG signals via at least one of low resolution electromagnetic tomography (LORETA) and a cortical current density source model, and analyze the source-level EEG signals to sequentially select the two or more brain regions.

4. The apparatus for detecting a brain fingerprint of claim 3,
wherein the processor is configured to analyze directional causal connectivity of the EEG signals over time between the selected two or more brain regions via Granger causality method to detect causal connectivity between the selected two or more brain regions.

5. The apparatus for detecting a brain fingerprint of claim 1, wherein
the processor is configured to control the visual stimuli to be displayed on a display,
the visual stimuli include a grid-shaped flickering line array including a plurality of lines respectively flickering at predetermined flickering frequencies and two or more lines arranged in a grid shape, and the lines in the line array flicker at different flickering frequencies from each other, and
the EEG signals are induced when the subject selectively attends to a line combination of the line array while conceiving of any one of predetermined shapes.

6. The apparatus for detecting a brain fingerprint of claim 1, further comprising:
a brainwave detector configured to measure EEG signals of the subject,
wherein the brainwave detector is configured to measure a steady state visual evoked potential (SSVEP).

7. A method for detecting a brain fingerprint using the apparatus for detecting a brain fingerprint of claim 1, comprising:
detecting causal connectivity between two or more brain regions among a plurality of brain regions on the basis of EEG signals of a subject who selectively attends to at least a part of visual stimuli;
determining a brain fingerprint of the subject by recognizing an activation pattern of causal connectivity between brain regions on the basis of the detected causal connectivity;
identifying the subject based on the determined brain fingerprint;
determining whether or not the subject is a permitted user on the basis of the identified brain fingerprint of the subject; and
transmitting an authentication signal to a linked security device if the subject is a permitted user;
wherein the detecting of causal connectivity between two or more brain regions includes:
performing an EEG source localization analysis on the basis of the EEG signals measured from the plurality of the brain regions, and sequentially selecting two or more brain regions having the highest causal connectivity from activated brain region among the plurality of the brain regions.

8. The method for detecting a brain fingerprint of claim 7, wherein the identifying of the subject includes:
classifying the activation pattern of casual connectivity between brain regions of the subject by a classifier which is previously machine-learned based on already-acquired activation patterns of casual connectivity between brain regions which are labeled for a predetermined condition to each of a plurality of subjects, wherein the predetermined condition includes the generation of a predetermined brainwave via visual stimuli, and
distinguishing a registered user or a new user based on the result of classification or identifying a user corresponding to the subject among already registered users based on the result of classification.

9. The method for detecting a brain fingerprint of claim 7, wherein in the sequentially selecting of two or more brain regions,
the EEG signals measured from the plurality of the brain regions are analyzed via at least one of low resolution electromagnetic tomography (LORETA) and a cortical current density source model to sequentially select the two or more brain regions.

10. The method for detecting a brain fingerprint of claim 9,
wherein in the sequentially selecting of two or more brain regions,
directional causal connectivity of the EEG signals over time between the selected two or more brain regions is analyzed via Granger causality method to detect causal connectivity between the selected two or more brain regions.

11. The method for detecting a brain fingerprint of claim 7,
wherein the visual stimuli include a grid-shaped flickering line array including a plurality of lines respectively flickering at predetermined flickering frequencies and two or more lines arranged in a grid shape, and the lines in the line array flicker at different flickering frequencies from each other, and
the EEG signals are induced when the subject selectively attends to a line combination of the line array while conceiving of any one of predetermined shapes or letters.

* * * * *